(12) United States Patent
Roemisch et al.

(10) Patent No.: US 7,829,095 B2
(45) Date of Patent: Nov. 9, 2010

(54) INHIBITORY MONOCLONAL ANTIBODY AGAINST BLOOD CLOTTING FACTOR VII-ACTIVATING PROTEASE

(75) Inventors: Juergen Roemisch, Vösendorf (DE); Wiegand Lang, Coelbe (DE); Annette Feussner, Marburg (DE); Gudrun Muth-Naumann, Wetter (DE); Hans-Arnold Stoehr, Wetter (DE); Christian Kannemaier, Giessen (DE); Klaus Preissner, Giessen (DE); Fumie Nakazawa, Tokyo (JP)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 10/359,704

(22) Filed: Feb. 7, 2003

(65) Prior Publication Data

US 2003/0215447 A1 Nov. 20, 2003

(30) Foreign Application Priority Data

Feb. 8, 2002 (DE) ................................ 102 05 520

(51) Int. Cl.
*A61K 39/395* (2006.01)
(52) U.S. Cl. .............. 424/146.1; 424/141.1; 424/145.1; 530/388.25; 530/388.26; 435/337; 435/338
(58) Field of Classification Search .............. 530/388.1, 530/388.25; 424/141.1, 145.1
See application file for complete search history.

(56) References Cited

U.S. PATENT DOCUMENTS

| | | | |
|---|---|---|---|
| 5,175,087 A | 12/1992 | Ranby et al. | |
| 5,658,568 A * | 8/1997 | Bagshawe ................ | 424/134.1 |
| 5,968,759 A | 10/1999 | Roemisch et al. | |
| 6,528,299 B1 | 3/2003 | Römisch et al. ............. | 435/219 |
| 6,831,167 B2 * | 12/2004 | Becker et al. .............. | 536/23.2 |
| 2002/0110552 A1 | 8/2002 | Roemisch et al. | |
| 2003/0077271 A1 | 4/2003 | Kannemeier et al. | |
| 2003/0124622 A1 | 7/2003 | Roemisch et al. | |
| 2003/0125247 A1* | 7/2003 | Rosen et al. .................. | 514/12 |
| 2004/0083187 A1 | 4/2004 | Andreoli et al. | |
| 2004/0186277 A1 | 9/2004 | Roemisch et al. | |
| 2005/0032109 A1 | 2/2005 | Roemisch et al. | |
| 2005/0202002 A1 | 9/2005 | Roemisch et al. | |

FOREIGN PATENT DOCUMENTS

| | | |
|---|---|---|
| DE | 199 26 531.3 | 6/1999 |
| DE | 199 03 693 A1 | 10/1999 |
| DE | 199 37 218 A1 | 2/2001 |
| DE | 199 37 219 A1 | 2/2001 |
| DE | 100 36 641 A1 | 2/2002 |
| DE | 100 52 319 A1 | 4/2002 |
| DE | 100 23 923 A1 | 12/2002 |
| EP | 0 952 215 A2 | 10/1999 |
| EP | 1 059 359 A2 | 12/2000 |
| EP | 1 074 615 A1 | 2/2001 |
| EP | 1 074 616 A1 | 2/2001 |
| EP | 1 182 258 A1 | 2/2002 |

OTHER PUBLICATIONS

Choi-Miura et al., "Proteolytic activation and inactivation of the serine protease activity of plasma hyaluronan binding protein," 2001, Biol. Pharm. Bull. 24:448-452.*

Choi-Miura, "Novel human plasma proteins, IHRP (acute phase protein) and PHBP (serine protease), which bind glycosaminoglycans," 2004, Curr. Med. Chem. Cardiovascular and hematological Agents 2:239-248.*

Kipriyanov et al., "Generation of recombinant Antibodies," Molecular Biotechnology, 1999, 12:173-201.*

Romisch et al., "Quantitation of the factor VII and single chain plasminogen activator-activating protease in plasma of healthy subjects," Blood Coagulation and Fibrinolysis, 2001, 12:375-383.*

K. Laake et al., "Activation of Purified Plasma Factor VII by Human Plasmin, Plasma Kallikrein, And Activated Components of the Human Intrinsic Blood Coagulation System," *Thrombosis Research*, vol. 5 (6): 759-772 (1974).

N-H. Choi-Miura, et al., "Purification and Characterization of a Novel Hyaluronan-Binding Protein (PHBP) From Human Plasma: It Has Three EGF, a Kringle and a Serine Protease Domain, Similar to Hepatocyte Growth Factor Activator," *J. Biochem*, vol. 119 (6): 1157-1165 (1996).

K. Hashimoto et al., "Cloning of the cDNA for a Mouse Homologue of Human PHBP: A Novel Hyaluronan-Binding Protein," *Biol. Pharm. Bulletin*, vol. 20(11): 1127-1130 (1997).

J. Sumiya et al., "Isolation and Characterization of the Plasma Hyaluronan-Binding Protein (PHBP) Gene (HABP2)," *J. Biochem.*, vol. 122: 983-990 (1997).

(Continued)

*Primary Examiner*—Michael Szperka
(74) *Attorney, Agent, or Firm*—Finnegan, Henderson, Farabow, Garrett & Dunner, L.L.P.

(57) ABSTRACT

A monoclonal antibody which inhibits the blood clotting factor VII-activating protease and its proenzyme and a blood clotting factor VII-activating protease, stabilized by the addition of said monoclonal antibody, and its proenzyme are described. A suitable monoclonal antibody is produced by hybridoma cell line DSM ACC 2533. The application of the inhibitory, monoclonal antibody in the stabilization of blood clotting preparations and in preparations for reducing the coagulability of the blood is disclosed.

2 Claims, No Drawings

OTHER PUBLICATIONS

J. Roemisch et al., "A Protease Isolated From Plasma Which Activates FVII In a Tissue Factor Independent Manner But Inactivates FV and FVIII," *Annals of Hematology*, vol. 78 (1) Suppl. 1 (Abstract) (1999).

M. Etscheid et al.,43rd Annual Meeting of the GTH; Supplement I to vol. 78 A42, P030, (1999).

A. Hunfeld et al., "Detection of a Novel Plasma Serine Protease During Purification of Vitamin K-Dependent Coagulation Factors," *FEBS Letters*, vol. 1 (456): 290-294 (1999).

J. Roemisch et al., "A Protease Isolated From Human Plasma Activating Factor VII Independent of Tissue Factor," *Blood Coagulation and Fibrinolysis*, vol. 10 (8): 471-479 (1999).

J. Roemisch et al., "The FVII Activating Protease Cleaves Single-Chain Plasminogen Activators," *Haemostasis*, vol. 29: 292-299 (1999).

J. Roemisch et al., "The FVII Activating Protease Mediates Fibrinolytic Effects Activating Single-Chain Plasminogen Activators," *Annals of Hematology*, vol. 78 (1): 24-27 (Abstract) (1999).

A. Vostrov et al., "Plasma Hyaluronan-binding Protein Is a Serine Protease," *J. Biological Chemistry*, vol. 275 (30): 22978-22985 (2000).

C. Kannemeier et al., "Factor VII and Single-Chain Plaminogen Activator-Activating Protease: Activation and Autoactivation of the Proenzyme," *Eur. J. Biochem.*, 268: 3789-3796 (2001).

J. Roemisch et al., "Factor VII Activating Protease (FSAP): A Novel Protease in Hemostasis," *Biol. Chem.*, 383: 119-1124 (2002).

Derwent Abstract of EP 1 074 615, 2001.

Derwent Abstract of EP 1 074 616, 2001.

Derwent Abstract of EP 1 182 258, 2001.

\* cited by examiner

INHIBITORY MONOCLONAL ANTIBODY AGAINST BLOOD CLOTTING FACTOR VII-ACTIVATING PROTEASE

The invention relates to a monoclonal antibody which inhibits specifically the factor VII-activating protease or its proenzyme but which does not impair the proteolytic properties of other proteases.

It is known that proteases have a crucial function in the release of active enzymes from their precursors, the proenzymes, in the organism. In addition, however, proteases also have the property of degrading activated enzymes again which therefore frequently become inactive again after only a short time. In order to prepare stabilized pharmaceutical preparations, it is therefore frequently necessary to inhibit the activity of specific proteases.

The stabilization against degradation caused by proteases is therefore an important task also in the case of pharmaceutical preparations containing blood clotting factors, in order to ensure the effectiveness of such preparations, in particular even after a relatively long storage period.

The blood clotting system comprises two different, cascade-like activation pathways of clotting factors present in the plasma. Depending on the triggering mechanism, either the endogenous or the exogenous route preferably serves to initiate clotting.

In a tissue injury, thromboplastin (tissue factor, TF) is exposed on surfaces as an initiator of the exogenous clotting route. The clotting factor VII (FVII), as well as circulating, activated FVII (FVIIa), is bound to the membrane-bound thromboplastin. In the presence of calcium ions and lipids, this TF-FVIIa complex leads to the binding of FX which is converted into its activated form (FXa) by limited proteolysis. By activation of prothrombin to thrombin, FXa in turn leads to the formation of fibrin and thus finally to wound closure.

FVIIa is found in very low concentrations in the plasma of healthy people. As yet, only very little is known about the cause and origin of the FVIIa circulating in the blood. Traces of expressed thromboplastin or thromboplastin released during cell destruction could play a part here.

The German laid-open specification 199 03 693 discloses an FVII-activating protease which is also referred to as FSAP (Factor Seven-Activating Protease). Owing to this property, FSAP can accelerate blood clotting and be applied as a pharmaceutical to hemorrhagic complications.

FSAP is present in the blood plasma as a proenzyme (single-chain FSAP, scFSAP). Using known chromatographic methods, it is possible to obtain mainly only the two-chain activated form of the protease (two-chain FSAP, tcFSAP), since the proenzyme is activated during the preparation. This activation may be caused by other proteases such as urokinase but may also occur autocatalytically. Activated FSAP can inactivate itself proteolytically. The preparation of scFSAP, in particular, is therefore difficult, but preparation of the intact tcFSAP is also not simple. Optimized methods for preparing FSAP have been described in German laid-open specifications 199 37 218 and 199 37 219. An important method step in this connection is immunoadsorption to matrix-coupled, monoclonal antibodies and specific conditions for stabilizing the eluate. However, in immunoadsorption too, care must be taken to work quickly as possible in order to avoid the formation of even small amounts of tcFSAP. This is most successfully done by using specific monoclonal antibodies which prevent or reduce only the activation or autoactiviation of FSAP instead of polyvalent protease inhibitors such as aprotinin, C1-esterase inhibitor or α-2 antiplasmin in the preparation.

The invention therefore relates to a monoclonal antibody which inhibits the blood clotting factor VII-activating protease or its proenzyme. Particularly suitable for this purpose is the monoclonal antibody produced by hybridoma cell line DSM ACC 2533. If such a monoclonal antibody is added to blood clotting factor VII-activating protease or to its proenzyme, the latter are inhibited thereby. A factor VII preparation containing the abovementioned monoclonal antibody is stabilized due to inhibition of the factor VII-activating protease and its proenzyme.

The antibody of the invention may also be used for preparative and analytical applications. In fact, the German laid-open specification 199 03 693 discloses that FSAP has the property of inactivating during incubation the blood clotting factors VIII/VIIIa and V/Va in a manner which depends on the protease concentration and the incubation time. If the FSAP action is inhibited by the addition of the antibody of the invention, then this protects said blood clotting factors from proteolytic degradation. It is also possible to stabilize fibrinogen solutions by adding the antibody of the invention.

The inhibitory antibody of the invention opens up possible diagnostic uses by the fact that it is possible, when adding it to a protease-containing solution, to detect via selective inhibition of FSAP, whether the proteolytic action can be attributed to FSAP or to a different protease. This method may be applied in particular in all assay systems which are based on FSAP activity, for example the cleavage of chromogenic substrates, by activated FSAP or by measuring the amidolytic activity of FSAP-activated urokinase.

In addition, the inhibitory antibodies of the invention may also have direct prophylactic or therapeutic uses in the case of particular disorders. Thus, for example, an increase in the FSAP content in the plasma can increase the procoagulant properties of the blood and thus the risk of thrombosis. Administering an inhibitory antibody can reduce the coagulability of the blood and thus reduce the risk of thrombosis.

German laid-open specification 19 903 693 also mentions the particular fibrinolytic action of pharmaceutical preparations containing the blood factor VII-activating protease. Said protease may therefore also be used for the treatment of disorders caused by fibrin-containing thrombi. From this it follows that higher concentrations of FSAP may initiate or increase hemorrhagic tendencies which can be prevented or reduced by an inhibitory monoclonal antibody. This may also inhibit adverse effects on wound healing or the development of cancer.

The large variety of described possible applications of an inhibitory monoclonal antibody against FSAP are achieved by said antibody preventing activation of scFSAP and thus subsequent formation of tcFSAP. Since many of the previously known properties of FSAP are mediated by tcFSAP, inhibition of scFSAP is sufficient in order to block FSAP actions.

The monoclonal antibody obtained according to the invention from hybridoma cells DSM ACC 2533, therefore very effectively inhibits tcFSAP activity but also scFSAP autoactivation. Of course, this monoclonal antibody must still be humanized prior to application as a prophylactic or therapeutic agent in humans. These methods are well known and are not intended to be described here in detail.

Moreover, German patent application 100 52 319.6 has already described that, besides the blood clotting factor VII-activating protease (FSAP), in 5 to 10% of all blood donors tested there is an FSAP mutant which is inactive with respect to scuPA activation and whose amino acid sequence exhibits a Glu/Gln exchange and Gly/Glu exchange at amino acid position 393. This single-nucleotide polymorphism (=SNP)

is associated with a reduction in the activation of proplasminogen activators and thus with a reduced fibrinolytic potential and with an increased risk of thrombosis. In order to reduce this risk, European patent application 01 115 691.6 proposes the administration of wildtype FSAP.

The present invention now provides the further possibility of inhibiting FSAP and thus also the mutant by administering an inhibitory monoclonal antibody, thereby reducing the thrombotic or thromboembolic potential. On the other hand, FSAP mutants whose FVII-activating properties are reduced but whose fibrinolytic capacity is increased may be used for the treatment of potentially increased hemorrhagic tendencies by administering a monoclonal, inhibitory antibody of the invention.

The hybridoma cell line DSM ACC 2533 was identified and prepared as follows: 3 mice were immunized with FSAP. The spleen cells from one mouse were fused with the murine myeloma cell line SP2/0-Ag 0.14, using polyethylene glycol 4,000 as fusion reagent. The cells were distributed onto 24-well culture plates. The medium used was Dulbecco mod. Eagle's Medium containing 10% fetal calf serum and HAT for selection. After approximately 2 weeks, the growing cell clones were transferred to the wells of a 48-well culture plate and coded. The supernatant of 1,728 cell clones grown was assayed for the presence of mouse IgG by means of an ELISA. Mouse-IgG-positive supernatants were tested for specificity with the aid of immobilized FSAP. 108 of the clones assayed were identified as being specific for FSAP. Further experiments reviewed the inhibitory property of the monoclonal antibody from hybridoma cell line DSM ACC 2533. The antibody is of the IgG1 type.

The monoclonal antibody from hybridoma cell line DSM ACC 2533 inhibits the proteolytic activity of tcFSAP. Accordingly, not only does it inhibit the ability of FSAP to activate factor VII or prourokinase but also prevents FSAP autoactivation.

The following examples further illustrate the invention:

EXAMPLE 1

Studying the Effect of the Monoclonal Antibody from DSM ACC 2533 on (Auto)Activation of scFSAP Recalcification of citrate plasma activates coagulation and finally leads to the formation of a fibrin clot. Under these circumstances, scFSAP is activated only after a long delay, if at all. By simulating "contact activators" or reactive surfaces via the addition of dextran sulfate, scFSAP is also activated in the plasma milieu. This can be illustrated very clearly on the basis of SDS-PAGE and Western blot analyses. For this purpose, the recalcified sample to which dextran sulfate has been added is incubated for different times and then subjected to a "euglobulin" precipitation familiar to the skilled worker, in order to be able to carry out the subsequent SDS-PAGE in the best possible way. In this way, the protein concentration of the samples is lowered and the smearing of band patterns is prevented. A reducing agent is added to the samples obtained in this way, in order to identify more easily the heavy and light tcFSAP chains resulting from scFSAP activation. After transferring the band patterns obtained by SDS-PAGE to nitrocellulose (blotting), the labeled, monoclonal antibodies DSM ACC 2453 and DSM ACC 2454 described in German patent application 100 36 641.4 are used for detecting the two tcFSAP bands.

As a result of this experiment, the disappearance of scFSAP on the blot and the increase in the two tcFSAP chains are observed. Occasionally, it is also possible that only the heavy chain becomes visible, since the tcFSAP light chain contains the active site of FSAP and, during the incubation of the plasma, reacts with corresponding inhibitor proteins such as C1-esterase inhibitor or α-2 antiplasmin and finally, as a (quasi covalent) complex, is recognized by the detecting, monoclonal antibody with more difficulty.

If the monoclonal antibody obtained from DSM ACC 2533 is added to the above-described plasma sample and if scFSAP activation is detected as described above, disappearance of the high molecular weight (one-chain form) band and, correspondingly, appearance of the heavy (and light) chain(s) of tcFSAP are not observed, in contrast to the control (without said monoclonal antibody or with a noninhibitory, monoclonal antibody). Thus, the monoclonal antibody from the hybridoma cell line of DSM. ACC 2533 has bound to scFSAP, thereby preventing scFSAP activation.

The titration of this effect indicates that said antibody is a highly potent, monoclonal antibody for inhibiting scFSAP activation. Even amounts equimolar to FSAP significantly reduce activation, and this renders this inhibitory, monoclonal antibody a very valuable diagnostic and preparative excipient. The high effectivity at relatively low concentration makes a potential use of this monoclonal antibody for administration in humans attractive.

EXAMPLE 2

Inhibition of the Active tcFSAP by the Inhibitory, Monoclonal Antibody from Hybridoma Cell Line DSM ACC 2533

As described in the German patent application 199 03 693 the activity of FSAP may be tested in various assay systems. In addition to the activation of plasminogen-activator proenzymes or of FVII with corresponding acceleration of coagulation, it is also possible, for example, to monitor the rate of inactivation of FV, FVIII, FIX or fibrinogen. In these assay systems, the inhibitory, monoclonal antibody of the invention was tested for its inhibitory properties.

The result is that the inhibitory, monoclonal antibody from hybridoma cell line DSM ACC 2533 inhibits in a potent manner the activity of tcFSAP toward the abovementioned blood clotting factor. This is also true for scFSAP whose activation to tcFSAP and thus its conversion to the amidolytically active form are prevented, as is shown in Example 1 above.

The invention claimed is:

1. A monoclonal antibody produced by hybridoma cell line DSM ACC 2533.

2. A hybridoma cell line deposited under accession number DSM ACC 2533.

* * * * *